United States Patent [19]

Spears et al.

[11] Patent Number: 5,567,316

[45] Date of Patent: Oct. 22, 1996

[54] PROCESS FOR RECOVERING METALS FROM SOLUTION UTILIZING METALLOPROTEIN AFFINITY CHROMATOGRAPHY

[75] Inventors: Dennis R. Spears; John B. Vincent, both of Tuscaloosa, Ala.

[73] Assignee: The United States of America as represented by the Secretary of the Interior, Washington, D.C.

[21] Appl. No.: 464,191

[22] Filed: Jun. 5, 1995

Related U.S. Application Data

[62] Division of Ser. No. 158,553, Nov. 29, 1993, Pat. No. 5,441,663.

[51] Int. Cl.$^6$ .................................................. B01D 15/08
[52] U.S. Cl. ........................ 210/635; 210/656; 210/679; 210/198.2; 210/502.1; 502/403
[58] Field of Search ................................. 210/635, 656, 210/659, 679, 198.2, 502.1; 502/403; 436/161

[56] References Cited

U.S. PATENT DOCUMENTS

| | | | |
|---|---|---|---|
| 4,021,368 | 5/1977 | Nemec | 502/403 |
| 4,285,819 | 8/1981 | Yen | 210/679 |
| 4,585,559 | 4/1986 | DeVoe | 210/679 |
| 4,752,398 | 6/1988 | Holbein | 210/679 |
| 4,876,232 | 10/1989 | Barkatt | 210/679 |
| 4,909,944 | 3/1990 | Jackson | 210/679 |
| 4,943,375 | 7/1990 | Bradshaw | 210/679 |
| 4,952,321 | 8/1990 | Bradshaw | 210/679 |
| 4,980,065 | 12/1990 | Hsu | 210/632 |
| 4,995,984 | 2/1991 | Barkatt | 210/679 |
| 5,084,389 | 11/1992 | Lakshmanan | 502/403 |
| 5,120,443 | 6/1992 | Bruening | 210/679 |
| 5,190,661 | 3/1993 | Bruening | 210/679 |
| 5,284,832 | 2/1994 | Ferrari | 530/410 |

FOREIGN PATENT DOCUMENTS

| | | | |
|---|---|---|---|
| 2212763 | 8/1990 | Japan | 502/403 |
| 347535 | 2/1991 | Japan | 502/403 |

*Primary Examiner*—Ernest G. Therkorn
*Attorney, Agent, or Firm*—E. Philip Koltos

[57] ABSTRACT

A process for recovering metals from an aqueous metal-ion bearing solution includes the steps of: (a) forming an affinity chromatography matrix by providing a metal bearing protein bound to an insoluble support material to form an immobilized metalloprotein material; (b) introducing into the affinity chromatography matrix a quantity of aqueous metal-containing solution having a pH, redox potential or other property properly adjusted to cause ions of a selected metal entrained within the solution to bind to the immobilized metalloprotein material; (c) washing the matrix with a first buffer which does not elute the metal ions of interest but does remove other species of metal entrained in the solution; and (d) applying a second buffer or solution of appropriate pH, redox potential or other property to the affinity chromatography matrix to elute the metal ions of interest from the immobilized metalloprotein material.

3 Claims, No Drawings

PROCESS FOR RECOVERING METALS FROM SOLUTION UTILIZING METALLOPROTEIN AFFINITY CHROMATOGRAPHY

STATEMENT OF GOVERNMENT INTEREST

The invention described herein may be manufactured and used by or for the Government of the United States of America for governmental purposes without the payment of any royalties thereon or therefor.

This is a Division of application Ser. No. 08/158,553, filed Nov. 29, 1993, now U.S. Pat. No. 5,441,6 .

BACKGROUND OF THE INVENTION

1. Field of the Invention

The present invention relates generally to a process for recovering metals from an aqueous metal-bearing solution and, more particularly, to a process which utilizes metalloproteins immobilized on an insoluble support to remove metal ions such as the main group, transition, lanthanide, and actinide ions from the aqueous metal-ion bearing solution.

2. Description of the Prior Art

Vast quantities of metal-contaminated water are generated annually in the industrial world. Additionally, a tremendous amount of metal-contaminated water from past industrial activities exists. These solutions, which are generated as a by-product or direct result of both conventional non-nuclear and nuclear processes, often contain a variety of metals which makes selective recovery difficult and uneconomical.

Presently-known methods for removing metals from aqueous wastewater streams involve techniques which are sometimes ineffective or expensive when low concentrations of metal ions (1–100mg/L) are involved. Methods known and utilized today are referred to in the art as chemical precipitation, ion-exchange, solvent extraction, electrochemical treatment, reverse osmosis and membrane technology methods.

A presently-known method which has presented an alternative to other known methods and shows some promise for removing low concentrations of metals from aqueous wastewater streams utilizes immobilized non-living biomass. With this method, procaryotic and eucaryotic cells are employed since they are capable of binding metal ions as a precursor to removing a metal of interest from the wastewater stream. This biomass method utilizes biomass components such as cell wall components, polysaccharides and cellular proteins. Since these materials bind metal ions for a variety of purposes in living organisms, they give dead biomass an appreciable ability to bind metal ions in a process for removing metal from an aqueous wastewater stream.

Each of the individual metal-binding components of biomass inherently has its own selectivity and affinity for metal ions. However, while some overall degree of selectivity and specificity for individual metal ions is possible with this process, the biomass material, because of its complex composition, has limitations in its degree of specificity. This lack of specificity causes each of the biomass components to adsorb multiple metal ions from a solution. Since each of the biomass components utilized adsorbs ions of more than one metal suspended in the wastewater stream, it is difficult to concentrate individual metal ions of interest from multiple metal ion-bearing solutions.

As seen from the foregoing, all presently-known processes for recovering metals from aqueous wastewater streams have their shortcomings. Therefore, there is a need for an improved process for removing metals and, more particularly, a selected metal of interest, from aqueous wastewater streams which overcomes both the inefficiency and metal selectivity problems associated with these known processes.

SUMMARY OF THE INVENTION

The present invention relates to a process for recovering metals from an aqueous metal-ion bearing solution, such as a wastewater stream, designed to satisfy the aforementioned needs. The process of the present invention utilizes metalloproteins immobilized on an insoluble support as an agent to remove metal ions of interest entrained in an aqueous metal-ion bearing solution. The use of immobilized metalloproteins permits the recovery of metal ions from streams at lower concentration levels than currently obtainable and permits a selective and quantitative recovery of these metal ions.

Accordingly, the present invention is directed to a process for recovering metals from an aqueous metal-ion bearing solution. The process comprises the steps of: (a) forming an affinity chromatography matrix by providing a metalloprotein bound to an insoluble support material to form an immobilized metalloprotein material; (b) placing within the affinity chromatography matrix a quantity of aqueous metal-containing solution with a suitable pH, redox potential or possessing some other agent or property to cause ions of a selected metal within the metal-containing solution to bind to the immobilized metalloprotein material; (c) washing the affinity chromatography matrix with a first buffer having a pH selected to remove from the affinity chromatography matrix especially all metals within the aqueous metal-containing solution except the ions of the selected metals which remain bound to the immobilized metalloprotein material; and (d) washing the affinity chromatography matrix with a second buffer solution having a pH selected to elute the ions of the selected metals from the immobilized metalloprotein material.

These and other features and advantages of the present invention will become apparent to those skilled in the art upon a reading of the following detailed description wherein there is described an illustrative embodiment of the invention.

DETAILED DESCRIPTION OF THE INVENTION

The present invention utilizes affinity chromatography to remove or recover a metal of interest from an aqueous metal-ion bearing solution. Affinity metal chromatography is operable to selectively and reversibly bind metal ions from an aqueous solution under a certain set of conditions and then release as a concentrated solution the metal ions of interest under a different set of conditions. Affinity chromatography is chromatography which utilizes a natural "biospecific" ligand immobilized to insoluble particles. The agents used to selectively bind the metal ions of interest are metal-binding proteins, i.e.—metalloproteins. Metalloproteins tightly bind metal ions in stoichiometric quantities. The metalloproteins of interest to the process of the present invention are generally but not exclusively metal-transport or metal-detoxifying agents in their natural environment.

In general, any immobilized metalloprotein for which conditions can be found to reversibly bind metal ions of interest under appropriate changes in environment is applicable to this invention. These agents display some of the greatest specificity known for binding of particular metal ions. Metal-transfer and metal-detoxifying and other metal binding proteins with rather subtle changes in their environment can be induced to release bound metal ions. Such changes include, but are not limited to, changes of pH or redox potential, depending on the specific protein. An example of these metalloproteins is the iron transport protein of mammals known as transferrin. By covalently binding transferrin to insoluble supports, as an example of metalloprotein affinity metal chromatography material can be prepared. Constructing a column of these support proteins in a columnar container results in an affinity chromatography column.

In general, the metalloprotein affinity metal chromatography column is utilized in the process of the present invention by (a) placing in the column a metalloprotein bound to an insoluble support material to form an immobilized metalloprotein compound; (b) introducing into the affinity chromatography column a quantity of aqueous metal-containing solution having a pH or redox potential properly adjusted to cause ions of a selected metal entrained within the solution to bind to the immobilized metalloprotein compound; (c) washing the column with a first buffer or other solution which does not elute the metal ions of interest but does remove other species of metal entrained in the solution; and (d) applying a second buffer or solution of appropriate pH, redox potential or other agent or property, to the affinity chromatography column to elute the metal ions of interest from the immobilized metalloprotein compound. With proper choice of conditions, the metal ions of interest elute as concentrated bands from the column. This process of the present invention is useful in the removal of transition metals, lanthanide, actinide and main group metals from aqueous metal-ion bearing solution.

In the process of the present invention, transferrin (2–2.7 g conalbumin, i.e.—egg white transferrin) was immobilized on 15 g cyanogen bromide-activated sepharose using standard procedures provided by the manufacturer. The transferrins are well studied, and the pH dependence of binding of many metal ions to the unsupported metalloproteins has been examined in detail. However, it is important to note that immobilized metalloproteins as described above have not heretofore been used to specifically bind and separate metals. The cyanogen-bromide method can be used to affix proteins to supports such as carbohydrate-based polymers, containing exposed —OH groups including carbohydrates (i.e.—sephadex, sepharose (an agarose-based polymer), cellulose, etc,), silica gel, alumina and porous glass such that immobilized metalloprotein affinity chromatography columns containing metalloproteins supported on these supports can be readily prepared. However, a number of other techniques for covalent attachment of proteins to solid supports are available. As an illustration of how the process of the present invention is operable to remove metals of interest from an aqueous metal-ion bearing solution, such as a wastewater stream, consideration should be drawn to the following example.

EXAMPLE

After equilibration with 0.10M $NaHCO_3$, pH 7.25 buffer, the affinity chromatography column described above is loaded with 50 mL of 35 ppm $Cu^{2+}$ as $CuSO_4*5H_2O$ in deionized water. After this solution is loaded, the column is washed with 20 column volumes (approximately 1 L) of pH 7.25 bicarbonate buffer to remove the effluent and to see if either copper or protein are released from the column. The effluent from the column at this point has a Cu concentration of less than 14 ppb. The copper is eluted from the column with 50 mM sodium citrate, pH 3.5 buffer. All of the copper is recovered. It is also of interest to note that upon loading the light blue copper solution onto the column, the column turns an intense yellow color. The column is thus self-indicating as the color vanishes upon elutriation of copper. The color arises from a tyrosine phenoxide to metal charge transfer band; many metals give rise to intensity colored transferrin complexes. The elution profile of the cupric ions is comprised of two concentrated bands. The bands which have almost equal area correspond to copper bound to the two slightly different metal-binding sites of transferrin. The affixing of the immobilized metalloprotein to the support may accent the difference between the sites.

The effect of other metal ions on copper binding has been examined. For example, the conalbumin column was treated in an identical fashion with a solution containing 36 ppm of $Cu^{2+}$ as $CuSO_4*5H_2O$ and 68 ppm of $Hg^{2+}$ as $HgCl_2$ in 50 mL of deionized water. Copper was removed to less than 14 ppb in the eluent while mercury concentrations were lowered to less than 1.1 ppb. Consequently, this provides an indication that in one step copper concentrations can be reduced by at least a factor of a thousand and mercury concentrations can be reduced by almost 5 orders of magnitude. Conversely, this implies that under non-optimized conditions, solutions containing at least 1.1 ppb of $Hg^{2+}$ can be concentrated by over 5 orders of magnitude as application of citrate elution buffer eluted $Hg^{2+}$ ions as a 162 ppm solution. Likewise, cupric ions could be concentrated over a thousand fold, eluting as a concentration of 42 ppm.

The binding of copper was also examined in the presence of iron which binds more tightly to the immobilized metalloproteins. Addition of 10 mg of $CuSO_4*5H_2O$ and 12 mg of $Fe(HO_3)_3*9H_2O$ in 50 mL deionized $H_2O$ results in the appearance of two colored bands on the column. An orange to pink band of iron-transferrin complex appears at the top of the affinity chromatography column, while most of the remainder of the column appears yellow from the presence of the copper-transferrin species. Neither ion elutes when the column is washed with $NaHCO_3$ buffer; both are below detectable levels in the wash passed through the column. However, application of a citrate buffer at pH 3.5 results in the elution of both metals. The copper eluted first, being well separated from the iron which eluted last. Only 40 per cent of the iron eluted with the citrate buffer, the remaining iron was eluted by adding 10 mM EDTA to the citrate buffer and lowering the pH to 2.0. Thus, heavy metal ions can be separated by immobilized metalloproteins.

No measurable binding capacity was lost in three months of nearly continuous use during which time the column was exposed to pH's of between 2 and 11. The range of pH is limited by the pH stability range of the covalent protein-support linkage (pH 2–12) in the case of material supported via the CNBr method; for proteins other than transferrin, their stability could alter this range. The theoretical column capacity is two ions of metal per transferrin molecule bound to the support; this is also the observed capacity for cupric ions. Column capacity is measured by adding excess $CuSO_4*5H_2O$ to the column in the manner described above, washing the excess copper away with an $NaHCO_3$ buffer, and eluting and quantitating the remaining copper. Using quantities of copper close to the column capacity, cupric ions have eluted in concentrations as high as 1 ppt (part per thousand).

To examine the ability of the column to bind cupric and other ions from dilute solution, 8 L of tap water adjusted to pH 8 by the addition of solid $NaHCO_3$ was applied to the column. The concentrations of copper in the buffered tap water was below detection limits; however, after applying the $NaCO_3$ buffer wash and elution buffer (4 mM EDTA, 100 mM phosphate, pH 4.0), copper was removed at a concentration of 1.2 ppm, indicating a concentration of at least 2 orders of magnitude was possible. Other metals successfully concentrated by this method included iron, manganese, zinc, aluminum (main group metal) and tungsten. In contrast, the alkali metal potassium binds very weakly to the column and thus cannot be concentrated by this method.

In addition to what has been described above, some alternate embodiments of the conalbumin column have been demonstrated to work in the metal-recovery process of the present invention. For example, cyanide leach solution from a gold mine was adjusted to pH 8 and centrifuged to clarify it. Applying this solution to the affinity chromatography column (equilibrated to pH 7.25 with $NaHCO_3$ buffer), washing with bicarbonate buffer, and applying citrate elution buffer results in separation of cuprous and cupric ions from the original solution. The high cyanide concentration does not adversely affect the column. The binding and separation of metal ions (even different oxidations state ions of the same element) from saturated solutions suggests that the column is readily amendable to removal, concentration and separation of metal ions from seawater and other leach and related solutions.

At pH 8.0 (in the absence of buffered bicarbonate and carbonate), lanthanide ions (e.g.—$La^{3+}$, $Er^{3+}$, $Sm^{3+}$, $Ho^{3+}$) bind tightly to the affinity chromatography column. These ions can be eluted with 4 mM EDTA, 200 mM acetate and 200 mM phosphate buffer. Since $Er^{3+}$, and $Ho^{3+}$, have almost identical ionic radii to plutonium$^{4+}$(the form of plutonium stable in natural water), it is apparent the process of the present invention is also capable of being used to remove plutonium from an aqueous wastewater stream.

To test the feasibility of using the affinity chromatography column to decontaminate plutonium-bearing water, the binding of thorium as $Th^{4+}$ was first examined using a column matrix comprised of 2.0 g concalbumin immobilized on 15 g $CNB_r$ activated sepharose. This metal was chosen as its only stable ion is the tetravalent ion and the specific activity (Ci/g) of natural thorium is orders of magnitude lower than that of the predominate radioisotopes of plutonium. 26.0 mg of $Th(NO_3)_4*4H_2O$ was dissolved in 50 ml of HEPES (N-2-hydroxyethylpiperazine-N'-ethanesulfonic acid) buffer (0.010M, pH 7.35) and the resulting solution was applied to the affinity chromatography column equilibrated with HEPES buffer. The column was then washed with HEPES buffer. The metal ions were then eluted with pH 4 buffer containing 0.200M $NaH_2PO_4$, 0.200M NaOAc, and 0.004M EDTA. Thorium binds tightly to the column, and none of the metal was detected in the effluent while the column was being loaded or washed. Application of the OAc-$PO_4$-EDTA buffer completely removed the thorium from the column. This buffer had previously been shown to efficiently remove ferric ions from the column; however, ferric ions have a greater affinity for transferrin than any other transition metal examined.

The ionic radius of hexacoordinate $Pu^{4+}$ is approximately 86 pm; the trivalent lanthanide ions have similar ionic radii (i.e.—Lu, 86.1; Er, 89.o, etc.). Hence, trivalent lanthanide ions are often utilized as models of $Pu^{4+}$ and other similarly sized actinide ions. Holmium (90.1pm) was chosen to examine lanthanide binding. 45.3 g $Ho(NO_3)_3*5H_2O$ was dissolved in 50 mL of HEPES buffer (0.010M, pH 8.0), and the resulting solution was applied to the same column. The column was washed with 120 mL HEPES buffer; finally OAc-$PO_4$-EDTA buffer was applied to elute the metal ions. Again, the ion of interest is retained and eluted quantitatively. It is of note that the amount of holmium bound by the column exceeds the capacity of the supported transferrin. This represents the ability of the support itself to bind a small quantity of ions of large charge to size ratio. Lanthanide ions could also be eluted by applying the pH 8.0 HEPES buffer supplemented with 4 mm EDTA; therefore only an addition of chelating agent can be used to elute.

To demonstrate the ability to utilize metalloproteins other than transferrin and its relatives, 50,000 units of carboxypeptidase A (50 units/mg) were immobilized to 15 g cyanogen-bromide activated sepharose. As isolated, the protein contains zinc, which was removed by washing the matrix with 0.1M Tris (Tris-(hydroxymethyl)aminoethane), 0,002M 1,10—phenanthroline buffer, pH 5. The carboxypeptidase A column was adjusted to pH 7.0 with 0.10M Tris buffer. Solutions containing $Fe^{2+}$, $Co^{2+}$, $Cu^{2+}$, and $Zn^{2+}$ ions respectively, were applied to the column in an identical fashion to the transferrin columns. All ions bound to the column. In the case of $Co^{2+}$ and $Cu^{2+}$, the column was self-indicating turning a pink color and a blue-violet color, respectively, when the ions were bound. All four ions could be eluted from the column by applying a 0.1M Tris, 0,002M phenanthroline solution, pH 5.0. All four ions could also be eluted without the chelating agent (phenanthroline) using deionized water adjusted to pH 4 using hydrochloric acid.

As described, transferrin metalloprotein affinity metal chromatography provides an excellent means for the quantitative removal and recovery of trivalent lanthanide ions and thorium ions from an aqueous solution. This result suggests that immobilized metalloproteins may serve as agents for the decontamination of plutonium-bearing material. Of equal importance, the affinity metal chromatography method of the present invention has been shown as: (1) readily adaptable to be selective for a wide variety of metals by choice of specific metalloproteins, (2) versatile and adaptable to a wide variety of different conditions, including adsorption of the main group, transition and lanthanide/actinide metal ions at pH ranges of 2–12, followed by release in the range of pH 2–8, (3) amenable to metal ion removal in a soluble, concentrated form; and (4) amenable to metal ion removal at lower concentrations than other known methods.

It is thought that the present invention and many of its attendant advantages will be understood from the foregoing description and it will be apparent that various changes may be made in the form of the invention without departing from the spirit and scope of the invention or sacrificing all of its material advantages, the forms hereinbefore describe being merely preferred or exemplary embodiments thereof.

We claim:

1. A process for recovering metals from an aqueous metal-ion bearing solution, comprising the steps of:

(a) forming an affinity chromatography matrix by providing carboxypeptidase, a metalloprotein, bound to a carbohydrate-based support, an insoluble support material, to form an immobilized metalloprotein material;

(b) placing in contact with said affinity chromatography matrix a quantity of an aqueous metal-containing solution having a pH and ionic strength adjusted to cause selected metal ions within said aqueous metal-ion bearing solution to tightly bind to said immobilized metalloprotein material;

(c) placing in contact with said affinity chromatography matrix a quantity of an aqueous solution having a pH, ionic strength, and/or chelating agent to remove all metal ions within said aqueous metal-ion bearing solution except said selected metal ions tightly bound to said immobilized metalloprotein material; and (d) placing in contact with said affinity chromatography matrix a quantity of an aqueous solution having a pH, ionic strength, and/or chelating agent to remove said selected metal ions tightly bound to said immobilized metalloprotein material.

2. The process for recovering metals from an aqueous metal-bearing solution as recited in claim 1, wherein said carbohydrate-based support is an agarose-based polymer.

3. The process for recovering metals from an aqueous metal-bearing solution as recited in claim 2, wherein said agarose-based polymer is sepharose.

* * * * *